United States Patent [19]

Migliori et al.

[11] Patent Number: 4,976,148

[45] Date of Patent: Dec. 11, 1990

[54] RESONANT ULTRASOUND SPECTROMETER

[75] Inventors: Albert Migliori, Santa Fe; William M. Visscher, Los Alamos; Zachary Fisk, Santa Fe, all of N. Mex.

[73] Assignee: The United Stated of America as represented by the Department of Energy, Washington, D.C.

[21] Appl. No.: 406,007

[22] Filed: Sep. 12, 1989

[51] Int. Cl.$^5$ ............................................. G01N 29/12
[52] U.S. Cl. ...................................... 73/579; 310/327; 73/602; 364/508
[58] Field of Search ........................... 73/579, 571, 602; 364/508; 310/327

[56] References Cited

U.S. PATENT DOCUMENTS 4,607,341  8/1986  Monchalin .......................... 364/508

FOREIGN PATENT DOCUMENTS 0169726  7/1986  Japan ...................................... 73/579
0657313  4/1979  U.S.S.R. ................................. 73/579

OTHER PUBLICATIONS

I. Ohno, "Free Vibration of a Rectangular Parallelepiped Crystal and Its Application to Determination of Elastic Constants of Orthorhombic Crystals," 24 J. Phys. Earth, pp. 355-379 (1976).
T. Goto et al., "An Apparatus for Measuring Elastic Constants of Single Crystals by a Resonance Technique Up to 1,825 K." Unpublished (1988).

Primary Examiner—Hezron E. Williams
Assistant Examiner—Rose Finley
Attorney, Agent, or Firm—Ray G. Wilson; Paul D. Gaetjens; William R. Moser

[57] ABSTRACT

An ultrasound resonant spectrometer determines the resonant frequency spectrum of a rectangular parallelepiped sample of a high dissipation material over an expected resonant response frequency range. A sample holder structure grips corners of the sample between piezoelectric drive and receive transducers. Each transducer is mounted on a membrane for only weakly coupling the transducer to the holder structure and operatively contacts a material effective to remove system resonant responses at the transducer from the expected response range. i.e., either a material such as diamond to move the response frequencies above the range or a damping powder to preclude response within the range. A square-law detector amplifier receives the response signal and retransmits the signal on an isolated shield of connecting cabling to remove cabling capacitive effects. The amplifier also provides a substantially frequency independently voltage divider with the receive transducer. The spectrometer is extremely sensitive to enable low amplitude resonance to be detected for use in calculating the elastic constants of the high dissipation sample.

8 Claims, 7 Drawing Sheets

RESONANT ULTRASOUND SPECTROMETER

BACKGROUND OF THE INVENTION

This invention relates to acoustical measurements in solid materials and, more particularly, to the use of resonant ultrasound spectroscopy to determine a variety of material properties. This invention is the result of a contract with the Department of Energy (Contract No. W-7405-ENG-36).

The elastic properties of solid crystals, metals, alloys, ceramics, and glasses are some of the most basic data in the physical sciences. It has long been recognized that these intrinsic properties are related to the acoustic resonances exhibited by solid objects. Acoustic resonance data are also related to defects and sound dissipation properties of the material.

I. Ohno, "Free Vibration of a Rectangular Parallelepiped Crystal and its Application to Determination of Elastic Constants of Orthorhombic Crystals," 24 J. Phys. Earth, pp. 355-379 (1976), incorporated herein by reference, discusses the theory relating resonance frequency data of rectangular parallelepiped crystals to elastic constant determinations. Measurements and numerical algorithms have been obtained for very low dissipation materials where the elastic constants are already known to within a few percent or better.

In a conventional resonance measuring system, described by Ohno, a rectangular parallelepiped specimen is placed between two piezoelectric transducers. One of the transducers is excited by a sweep frequency synthesizer and the output signal from the other transducer is amplified and displayed as a function of exciting frequency. A spectrum of the sequence of resonance response peaks from the sample is determined for analysis. The specimen is placed in contact with the transducers on its corners as lightly as possible to preclude suppressing resonance peaks while avoiding resonance frequency shifts under increased specimen loading.

There are some problems with conventional resonance measuring systems which significantly impact the application to crystalline materials. Two of the problems are identified by T. Goto et al., "An Apparatus for Measuring Elastic Constants of Single Crystals by a Resonance Technique Up to 1,825K," unpublished (1978). When the transducer is in direct contact with the specimen, many normal vibrational frequencies of the transducer itself are superimposed on the resonant modes of the specimen. Goto did not detect this problem in the high temperature device described in the article, wherein buffer rods transmit the specimen response to remotely located transducers, because the sample resonances were very sharp. The resonant frequency shift, mentioned above, is also noted, along with a mention that the applied load cannot become too close to zero because some of the vibrational signals of the specimen would become too small to be detected. The solution was to maintain a 5 g load on the specimen.

These conditions have made the conventional procedures difficult to apply to high dissipation materials, such as some glasses, high temperature superconductors, composites, and also materials generally at temperatures below 100K, etc. For low dissipation materials, the transducer can be damped by bonding the transducers to high dissipation solids whereby the sample response amplitudes are sufficiently greater than spurious resonant responses from the mechanical system that the specimen responses can be readily distinguished. For higher dissipation materials, the spurious resonances have amplitudes as large as the sample response amplitudes. These extra frequencies make the numerical analysis difficult to implement. Beat frequencies also occur, destroying the shape of the sample resonances.

Further, highly dissipative materials (low Q) produce weak signals. Conventional detectors, i.e., diode detectors, introduce a dead zone for signals having a strength below 0.6 V, obscuring the response shapes. Merely increasing the drive level introduces further inaccuracies from non-linear and heating effects. The problem of weak signals is compounded by the capacitive nature of the transducers. Conventional amplifiers have an input impedance which, in combination with the impedance of the transducer and connecting cable, provides an RC rolloff in the frequency range of interest to produce a strongly frequency dependent system gain, obscuring the low frequency resonances.

These and other problems of the prior art are addressed by the present invention and an improved resonance spectrometer is provided which can be used with high dissipation materials. Accordingly, it is an object of the present invention to enable the measurement of resonant frequencies of high dissipation materials.

It is another object of the present invention to provide a transducer which is mounted to substantially eliminate system resonant response signals at frequencies within the expected sample resonance range.

One other object of the present invention is to minimize input signal losses to the signal amplifier.

Yet another object of the present invention is to produce accurate representations of sample resonance shapes.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF INVENTION

To achieve the foregoing and other objects, and in accordance with the purposes of the present invention, as embodied and broadly described herein, the apparatus of this invention may comprise an ultrasound resonant spectrometer for use with a rectangular parallelepiped sample of a high dissipation material having an expected resonant response frequency range. A sample holder structure contacts corner portions of the sample with a drive transducer assembly and a receive transducer assembly mounted on the sample holder. The receive and drive transducer assemblies derive an output response of the sample from the receive transducer assembly as the drive transducer assembly excites the sample over the expected resonant response frequency range. A transducer is mounted on a thin membrane for weakly coupling the transducer to the sample holder structure. The transducer further operatively contacts a material effective to substantially remove system resonant responses at the transducer within the sample resonant response frequency range. A square-law detector amplifier amplifies the response signal output from the receive transducer while preserving the signal shape. A cable having a center signal conductor, a first shield isolated from ground, and a surrounding grounded second shield connects the receive transducer assembly with the amplifier. The amplifier includes a unity gain section for driving the isolated shield with a signal matching the signal on the signal conductor effective to eliminate capacitance effects from the cable and minimize signal loss.

In another aspect of the invention, an improved transducer assembly is provided for the receive and drive transducer assemblies in a resonant ultrasound spectroscopy system having a sample holder structure for contacting corner portions of a rectangular parallelepiped sample of a high dissipation material, where the receive transducer assembly and a drive transducer assembly contact the sample. The transducer assemblies include a transducer mounted on a thin membrane for weakly coupling the transducer to the sample holder structure. The transducer further operatively contacts a material effective to substantially remove system resonant responses at the transducer within the sample resonant response frequency range.

In yet another aspect of the present invention an amplifier, for use in an ultrasound resonant spectroscopy system having a sample holder structure with a drive transducer and a receive transducer for contacting corners of a rectangular parallelepiped sample for transmitting sample responses up to about 4 MHz, minimizes signal losses from the receive transducer and preserves the sample resonant response shape. The amplifier has a unity gain input amplifier for driving an isolated shield surrounding the signal conductor in a cable connecting the receive transducer to the amplifier with a signal matching the sample response signal on the signal conductor to effectively eliminate capacitance effects from the cable transmission.

BRIEF DESCRIPTION OF THE DRAWINGS

The accompanying drawings, which are incorporated in and form a part of the specification, illustrate embodiments of the present invention and, together with the description, serve to explain the principles of the invention. In the drawings.

DETAILED DESCRIPTION OF THE INVENTION

Figure 1:
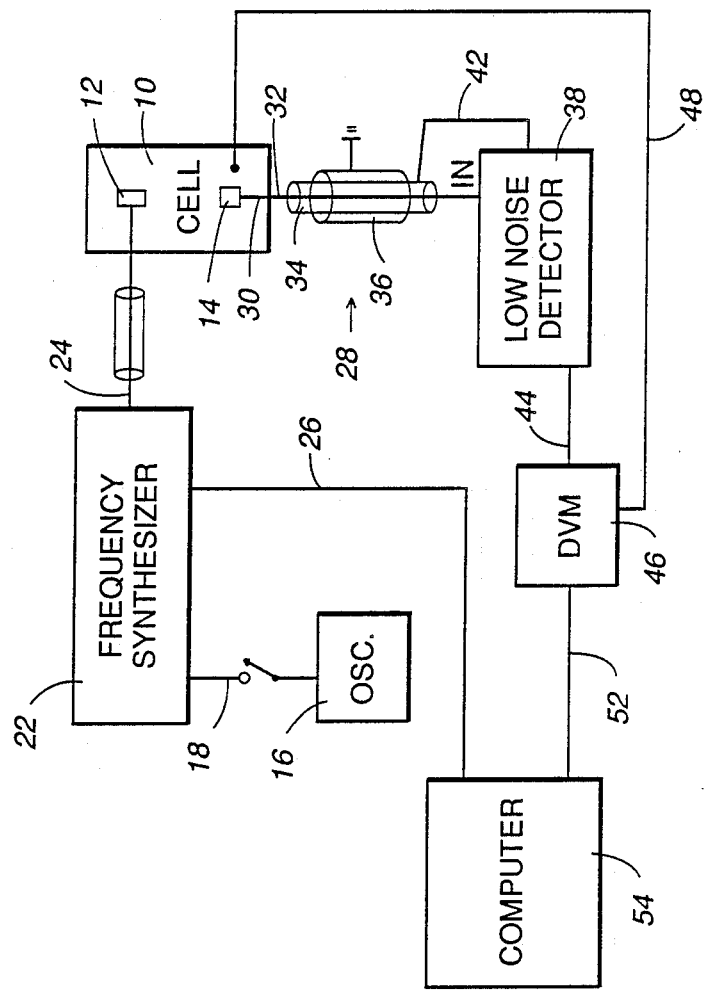
FIG. 1 is a schematic drawing in block diagram format of an ultrasound resonant spectrometer according to the present invention.

Referring now to FIG. 1, there is shown a schematic drawing of an ultrasound resonant spectrometer according to one embodiment of the present invention. Sample cell 10 includes drive transducer assembly 12 and receive transducer assembly 14 for receiving and holding a material sample therebetween for ultrasound resonant spectroscopy. Low frequency oscillator 16 generates a modulating output 18 for input to frequency synthesizer 22 to cause synthesizer 22 to generate a sweeping range of output frequencies 24 for input to drive transducer assembly 12. Transducer assembly 12 includes a transducer, typically a piezoelectric crystal, for vibrating a sample material (e.g., sample 62 in FIG. 3). As drive frequency 24 sweeps through frequencies which are resonant with a sample, an enhanced output 30 is produced by receive transducer assembly 14.

Figure 2:
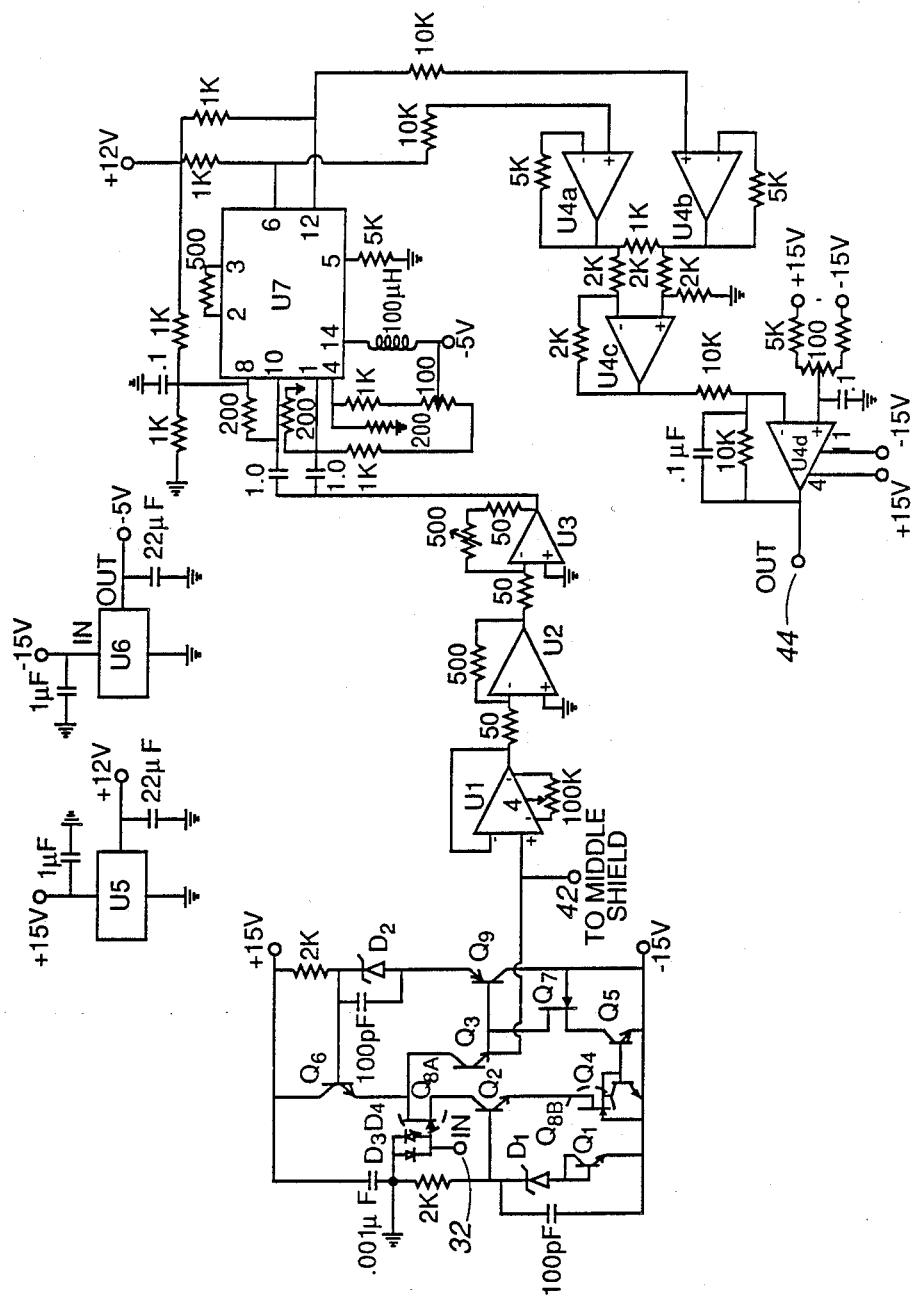
FIG. 2 is a schematic drawing of a low-noise detector for use in the system shown in FIG. 1.

Output signal 30 is passed along a conductor 32 to low noise detector 38 for generating square-law output signal 44. Detector 38, more particularly described with reference to FIG. 2, provides an input impedance which has a very high resistance and a low capacitance to form a voltage divider with the transducer capacitance which is frequency independent. If the detector input capacitance is lower than the capacitance of the transducer, the voltage divider ratio can be made close to unity. The frequency-independent voltage divider preserves the shapes and relationships of the sample resonant responses.

It will also be appreciated that the capacitance of the connecting cable 28 can significantly attenuate the strength of the signal 30 reaching detector 38. For example, a coaxial cable of length 2 meters may have a capacitance of 200 pF, providing an attenuation factor of about 25 dB for typical output signals from a receive transducer with a capacitance of about 10 pF. In accordance with the present invention, cable 28 includes center signal conductor 32, isolated shield 34, and grounded shield 36. Detector 38 further includes a unity gain input amplifier which outputs signal 42 to isolated shield 34. Signal 42 matches signal 30 on center conductor 32 to minimize the voltage difference between conductor 32 and shield 34, thereby eliminating the capacitance therebetween.

Signal 44 is output from detector 38 for input to digital voltmeter 46 to produce a digital output signal 52 for input to computer 54. A thermocouple signal 48 may also be output from sample cell 10 for use in processing the response data 44. Digital resonance signal 52 is input with synthesizer 22 output frequency signal 26 to computer 54 for developing a resonant response spectrum from the material sample. Computer 54 may also include software for processing the resonant spectrum to derive the material constants, i.e., the elastic constants, for the sample. The system shown in FIG. 1 produces an output signal 44 having a lorentzian shape with resonant responses limited to those of the material sample from which the elastic constants can be deduced.

A schematic diagram of a low-noise square-law detector for use in the ultrasound resonant spectroscopy system of FIG. 1 is shown in FIG. 2. The detector includes a unity gain input stage (components Q1–Q9) for inputting transducer signal on conductor 32 and outputting a matching signal 42 on isolated shield 34, operational amplifier stages (U1–U3), a communications demodulator (U7) having square-law output, and an instrumentation amplifier (U4a,b,c) with unity gain low-pass filter (U4d) to generate the analog output square-law signal 44. Circuits U5 and U6 provide the voltage supplies for demodulator U7.

In the unity gain amplifier stage, transistors Q8a and Q8b may be a matched JFET pair on a single substrate. Transistor Q8b has the source biased one diode drop voltage above the negative power supply (−15V) by the configuration of transistor Q4, and its gate is at the negative power supply voltage. Thus, transistor Q8b acts as a constant current source. The drain of transistor Q8b is driven at a constant voltage by transistor Q2, which is connected as an emitter-follower. Transistor Q2 is biased with the emitter one diode drop below the base and the base is one diode drop plus 5.0V above the negative power supply due to transistor Q1 and zener diode D1. This voltage is held constant and no RF is present whereby parasitic capacitance does not degrade performance. The current through transistor Q2, and therefore Q8a and Q6 is constant and equal to the current determined by the gate-source voltage of transistor Q8b.

Because of the constant current through transistor Q8a, the gate-source voltage is held at one diode drop. The signal input from signal conductor 32 is connected to the gate of transistor Q8a and sees the capacitance of transistor Q8a and static protection diodes D3, D4 (about 1.5 pF) and the practically infinite resistance of the transistor Q8a gate. Thus, the input characteristics provide the required capacitive voltage divider with the transducer which is independent of the frequency. The source voltage of transistor Q8a is one diode drop below the gate and tracks the input voltage exactly, providing a voltage follower, or unity gain, stage. The output from transistor Q8a source is input to current amplifier transistor Q3, connected as an emitter follower to provide the output signal at the emitter at a higher current.

Parasitic capacitance effects are eliminated by the action of transistors Q6, Q9, and zener diode D2 to maintain a constant drain-source voltage of 5.0V plus one diode drop across Q8a. Transistors Q4 and Q5 maintain a constant current through transistor Q7 equal to the current through transistor Q8a to fix the drain-source voltage of transistor Q7. Thus, transistor Q7 acts as a dynamic load for the output.

The output signal from transistor Q3 is output 42 to the isolated shield 34 of cable 28 (see FIG. 1) and also to unity-gain, operational amplifier buffer U1. Amplifier U1 then drives gain stages U2 and U3. In one embodiment, amplifiers U1, U2, U3 provide a voltage gain of 100 and a bandwidth of about 10 MHz. The amplified output is input to demodulator U7 which provides outputs at pins 6 and 12 which are the square of the inputs at pins 1 and 4, but out of phase with each other and 10.5V above ground. Amplifiers U4a,b,c form a conventional instrumentation amplifier which shifts the outputs of demodulator U7 to ground and subtracts the out-of-phase signal to produce a doubled output of the squared input referenced to ground. Amplifier U4d is connected to form a unity-gain, low-pass filter to remove the frequency-doubled component produced by demodulator U7. Output signal 44 is a dc signal exactly proportional to the square of the amplitude of the rf input signal 30 on conductor 32 at transistor Q8a. Output signal 44 is insensitive to phase and has a very low noise.

Preferred components for the circuit depicted in FIG. 2 are as follows:

| D1, D2 | 1N751A | Q1–Q6 | 2N2857 |
|---|---|---|---|
| U1–U3 | LM6361 | Q2 | 2N4416 |
| U4 | LM224 | Q8 | 2N3954A |
| U5 | 7812 | Q9 | 2N3251A |
| U6 | 7905 | | |
| U7 | MC1596G | | |

Figure 3:
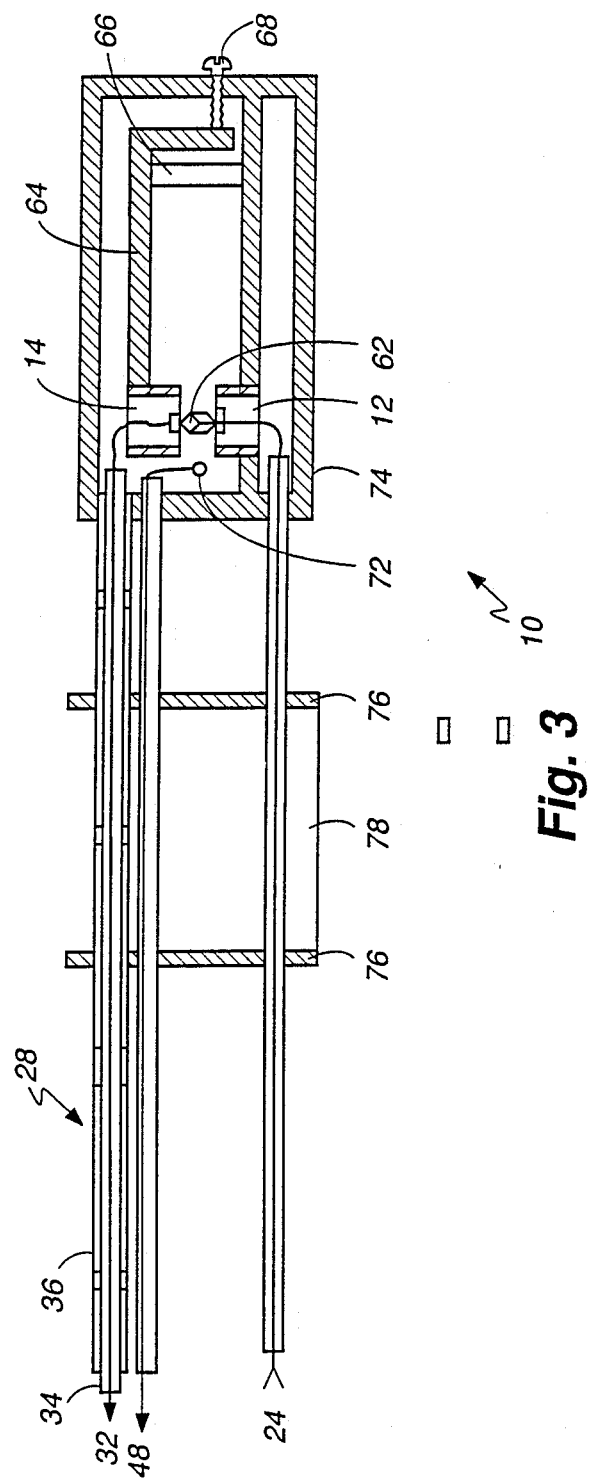
FIG. 3 is a pictorial illustration, in partial cross-section, of a transducer assembly for sample mounting.

Referring now to FIG. 3, there is shown, in partial cross-section, sample cell 10 for operation in a simple helium flow cryostat from 9K to 350K. Drive transducer assembly 12 is mounted within cell 10 and is electrically connected with sweeping output frequency signal 24 to drive material sample 62. Receive transducer assembly 14 is mounted on hinged arm 64, which pivots on needle bearing 66. The force applied to sample 62 is solely from the weight of arm 64 rather than springs, thereby enabling stable resonant frequencies from sample 62 as the temperature is varied. Loading screw 68 provides for adjustment during loading of the sample 62. The output signal from receive transducer 14 is transmitted through triaxial cable 28 along center conductor 32, with isolated shield 34 and grounded shield 36 for removing capacitance effects. Thermocouple 72 transmits temperature data signal 48. The transducer assemblies 12, 14 are shielded by rf shield 74 and copper shields 76 and insulation 78 reduce heat leaks to sample cell 10.

The design of transducer assemblies 12, 14, in accordance with the present invention, substantially removes any transducer response to system resonances within the expected range of sample resonances. This is particularly necessary for receive transducer assembly 14. In the FIG. 4 embodiment, the resonant frequency of the transducer assembly is increased beyond the expected sample resonance range. In the FIG. 5 embodiment, the transducer assembly is damped for resonant frequencies in the sample resonance range. In both cases, transducers 82, 102 are bonded, e.g., with Stycast 1266 epoxy, to flexible membranes 86, 106, which may be a 0.001 inch thick membrane of DuPont Kapton H-Film, which has been coated on one side with evaporated silver for electrical contact and rf shielding. Membranes 86, 106 are thin enough to prevent acoustic coupling between transducers 82, 102 and the mounting shells 84, 104, eliminating any transmission of cell 10 (FIG. 3) resonances. Transducers 82, 102 are electrically connected using ribbons 94, 112, which may be strips of 0.001 inch thick, 0.040 inch wide DuPont Kapton coated with a conductive material, such as silver. Coated ribbons 94, 112 have a low self-inductance and low mass to preclude self-induced electrical or mechanical resonances which can be associated with thin wires.

Figure 4:
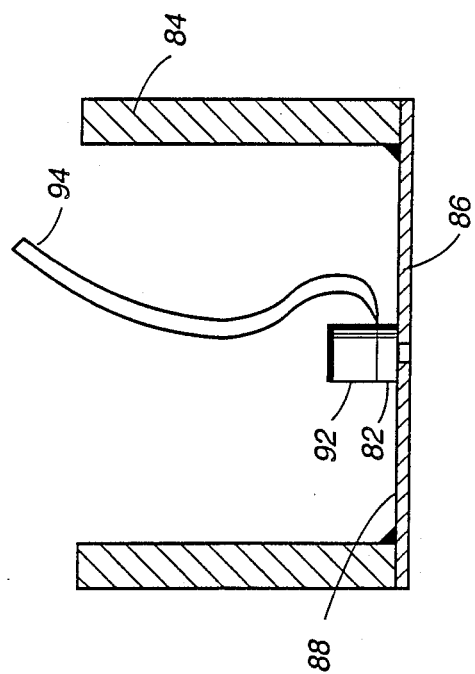
FIG. 4 is a cross-sectional view of one embodiment of a transducer according to the present invention.

Referring now to FIG. 4, transducer 82 is mounted below a cylinder 92 of material having a sound velocity much higher than the sample material in order to remove any system resonant response from the expected sample resonant responses. A material such as diamond (17 kM/s speed of sound) or beryllium (12 kM/s speed of sound) may be used. A diamond cylinder of 1.5 mm diameter and 1.0 mm length and bonded to membrane 86 has a lowest resonance at about 4 MHz and is a preferred material. Membrane 86 has an opening below transducer 82 to permit transducer 82 to contact a sample directly. The bonded cylinder approach has a very flat frequency response.

Figure 5:
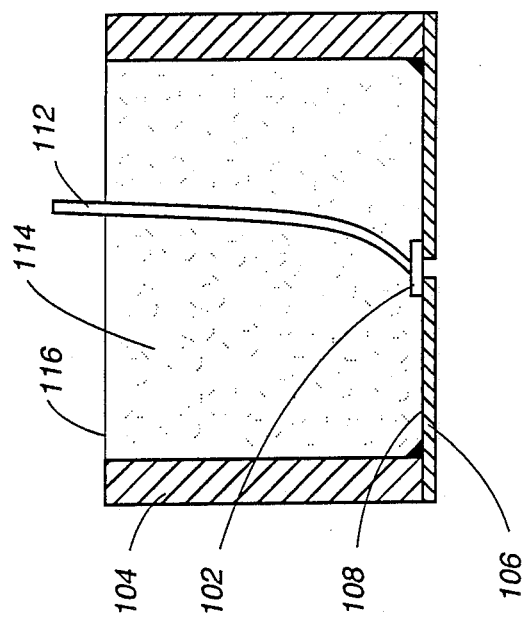
FIG. 5 is a cross-sectional view of a second embodiment of a transducer according to the present invention.

FIG. 5 shows a damped transducer 102 with a damping powder 114 filling mounting shell 104 above transducer 102. A powder 114 of 1 micron PbO has successfully damped frequencies above 1.2 MHz. The powder is held in place with a thin tissue cover 116. A suitable transducer, e.g., a 1.5 mm diameter lithium niobate transducer, has bending mode resonances which occur below 3 MHz which are, therefore, damped by powder 114. As shown in FIG. 4, membrane 106 also has an opening below transducer 102 to allow transducer 102 to contact the sample directly. It should be noted that the damped arrangement only reduces the amplitude of unwanted resonances, but the resulting very weak, broad resonances might still affect the output signal for very small sample signals and the diamond cylinder approach would be preferred in such instances.

Figure 6A:
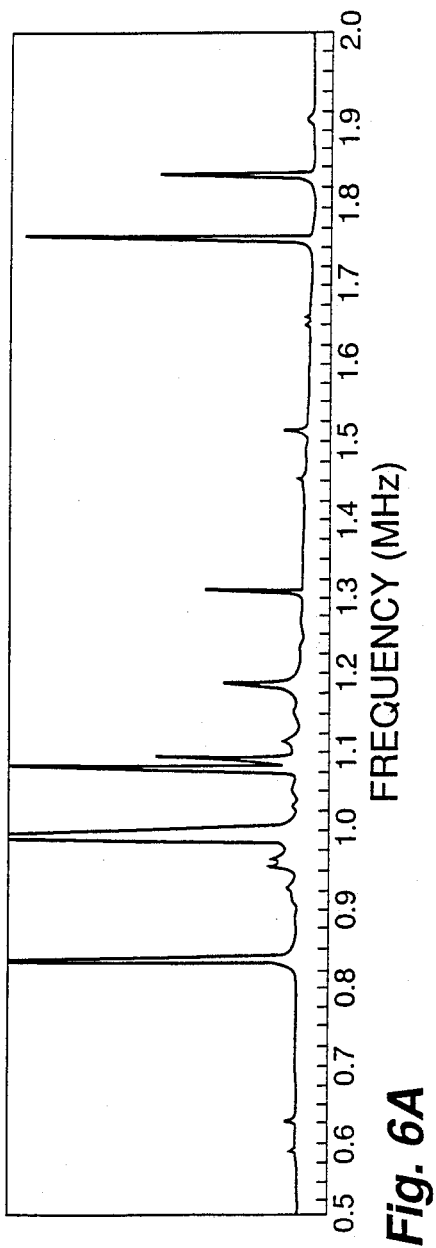
FIG. 6A is a response graph from $La_2CuO_4$ from 0.5–2.0 MHz.
Figure 6B:
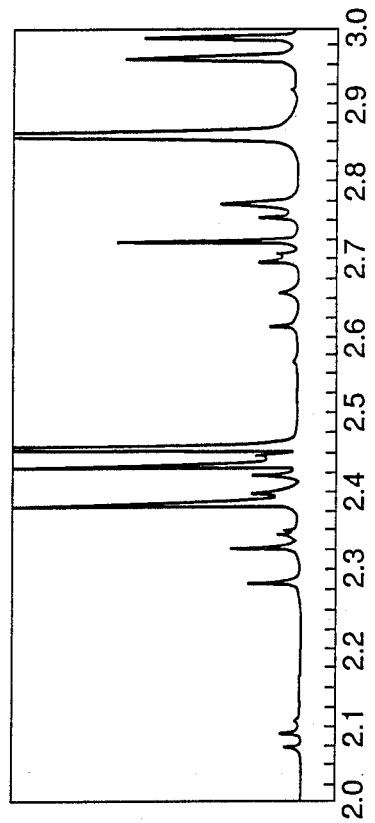
FIG. 6B is a response graph from $La_2CuO_4$ from 2.0–3.0 MHz.

FIGS. 6A and 6B are response graphs from a small single crystal of $La_2CuO_4$, a high dissipation, low Q material, using the apparatus of the present invention. The sensitivity of the apparatus is apparent from the number of small resonant responses detected by the apparatus, e.g., at about 1.3 MHz, 1.5 MHz, 2.1 MHz, 2.3 MHz, etc. All nine independent elastic constants were able to be determined from the response data using the analysis method hereinbelow discussed.

Figure 7:
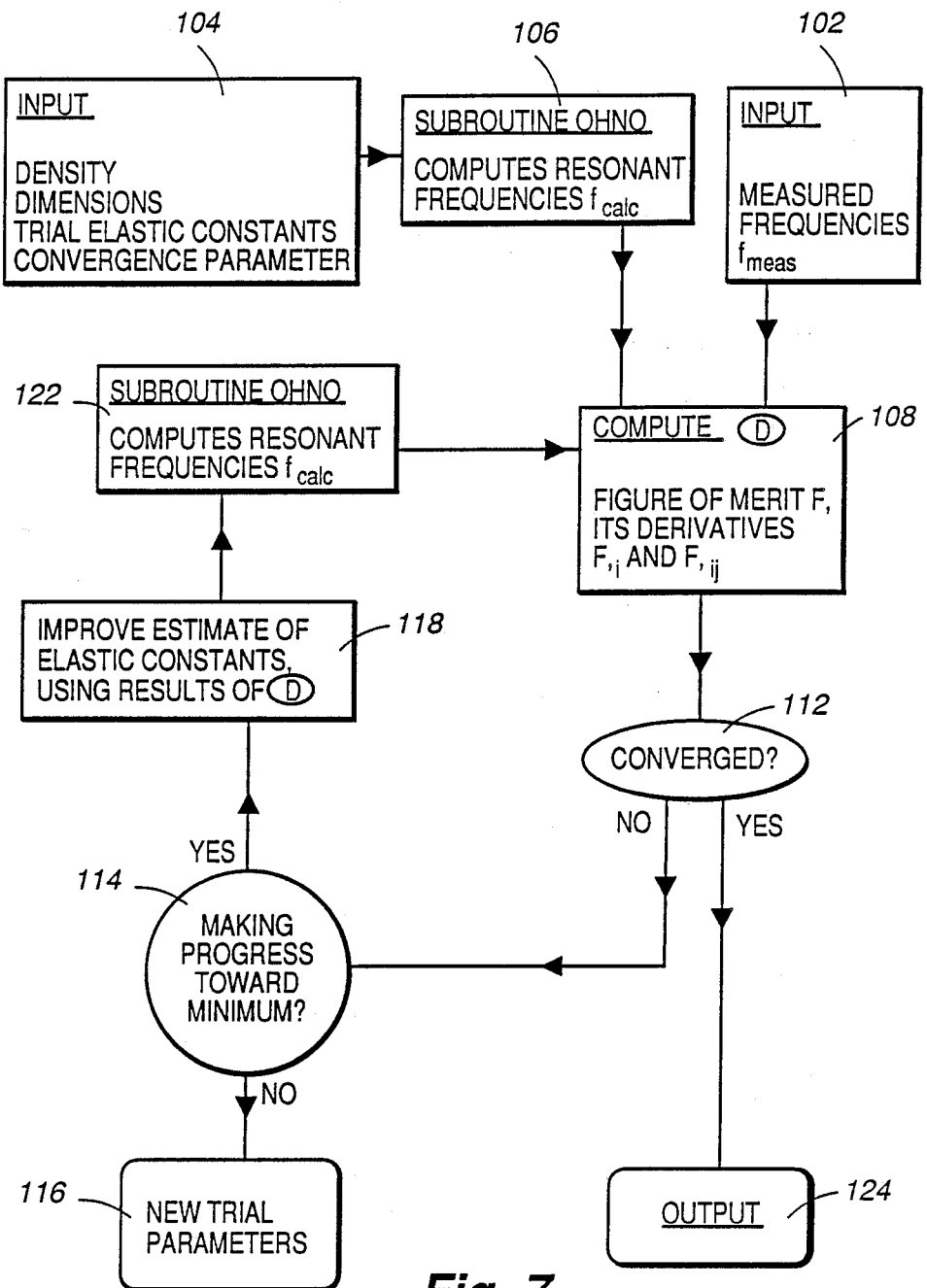
FIG. 7 is a flow diagram for determining elastic constants from resonant response data.

A flow diagram for deriving elastic constants from natural resonant response data is shown in FIG. 7. A program listing for implementing the flow diagram is provided in the appendix hereto. As developed by the Ohno publication, supra, it is straightforward to compute frequencies from elastic constants. Thus, the basic procedure of the process shown in FIG. 7 is to form a first estimate of the elastic constants, compute the expected resonant responses, compare the calculated response with the measured response, adjust the elastic constants, and repeat the process until a minimum difference exists.

The measured resonant response frequencies are input 102 to the program. Sample characteristics of density and dimensions, and an initial set of elastic constants determined from available sources, are input 104 to subroutine "Ohno" 106 for computing a resonant frequency spectrum from the trial parameters. A figure of merit F is computed 108 from the differences between the calculated and measured resonant response frequencies. The function F may be as simple as a sum of the squares or a more elaborate sum of Gaussians or Lorentzians.

The elastic constant space is then searched for the minimum of F using a minimization scheme, e.g., a conjugate-gradient algorithm such as provided by ZXCGS available from IMSL, Houston, Tex. The convergence criterion employed by ZXCGS is that the sum of the squares of the derivatives of F with respect to the independent variables, the elastic constants, becomes less than some predetermined number. If the data are converged 112, i.e., a minimum has been attained, the calculated elastic constants are output 124. It should be noted that the formation of F requires the assumption that there is a one-to-one correspondence between the measured and calculated resonance lines and that there are no missing or spurious resonance lines.

If F is not yet a minimum, the routine determines if F is progressing toward a minimum 114. If not, the routine ends 116 so a new set of trial parameters can be entered. Otherwise, the interim results 108 are used to improve the estimates for the elastic constants 118. The revised constants are then input to subroutine Ohno 122 for calculating a new set of resonant frequencies and a new figure of merit F is computed 108. The process is repeated until the routine determines that F has converged 112 on a set of elastic constants. If one set of elastic constants is determined at one temperature, that set can form the trial elastic constants for finding the constants at nearby temperatures to reduce the time for convergence.

Thus, a transducer assembly has been provided which does not introduce spurious resonances within the expected range of sample resonances. In one embodiment, transducer resonant frequencies and concomitant resonant responses are removed from the sample range and, in another embodiment, the transducer resonant responses are removed by damping. The transducer is weakly coupled to the sample cell assembly by a flexible membrane whereby apparatus resonances are not transmitted to the transducer. The resonant frequency responses of the sample can be clearly resolved for use in determining the sample characteristics of interest.

The foregoing description of the preferred embodiments of the invention have been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

APPENDIX PROGRAM LISTING

```
2        program tencut(input=tty,output=tty,tape6,tape2)
3   c
4   c this program minimizes the least-squares deviation of observed from
5   c calculated frequencies under variation of elastic constants.
6   c also the dimensions are optimizing variables. density remains constant,
7   c not mass.
8   c
9   c orders the calculated frequencies, maximizes the sum of lorentzians.
10  c
11         dimension h(100),gg(12),w(100),dev(50),temp(25)
12         common/o/ fr(8,50),dfr(8,50,12)
13       1 ,fex(50,25),kex(400),iex(400),wt(50,25),it
14         common /g/ d1,d2,d3, lb(200),mb(200),nb(200),x(12),rho
15         common /c/ wtc,c(9),ifunct
16         external funct
```

```
17   ***********************************************************
18   c following are data of 01/06/89.
19   ***********************************************************
20          data temp(1),(fex(i,1),i=1,50)/2.189,
21        1 .5909,.6309,.8405,.9880,.9980,1.0340
22        2 ,1.0724,1.0955,1.1841,1.3072,1.4537,1.4815,1.5030
23        3 ,1.5124,1.6404,1.6672,1.7538,1.8444,1.9047,0.0000
24        4 ,2.0700,2.0861,2.1153,2.2808,2.2868,2.3250,2.3362
25        5 ,2.3542,22*0./
26   c***********************************************************
27   c following are data from 02/9/89
28   c ***********************************************************
29          data temp(2),(fex(i,2),i=1,50)/2.989,
30        1 0.56044,0.63414,0.85001,0.00000,0.94792,
31        2 0.99067,1.06808,1.09454,1.14993,1.32962,
32        3 0.00000,0.00000,1.46355,1.48426,1.58699,
33        4 1.61576,1.77079,1.83707,1.85908,0.00000,
34        5 2.03631,2.05589,2.09155,2.28679,2.29467,
35        6 2.31320,2.34189,2.35834,2.36550,2.38111,
36        7 2.39512,2.44220,2.46625,2.48769,2.53927,15*0./
37   c ***********************************************************
38          data (wt(i,1),i=1,50)/28*1.,22*0./
39          data (wt(i,2),i=1,50)/35*1.,15*0./
40          data d1,d2,d3/.08625,.08810,.03490/
41          data c/1.6222,1.7323,2.0514,.52435,.75047,.84867,
42        1 .62556,.69898,.98416/
43          data nt,acc,dfpr0,wtc,width/1,1.e-7,.002,0.,1./
44          if(nt.le.0) call exit
45          do 10 it=1,2
46          dfpred=dfpr0
47          ifunct=0
48          do 33 i=1,50
49    33    wt(i,it)=wt(i,it)*width
50          do 32 j=1,9
51    32    x(j)=c(j)
52          x(10)=d1
53          x(11)=d2
54          x(12)=d3
55   c
56   c now we are ready to minimize residual
57   c
58          call zxcgr(funct,9,acc,75,dfpred,x,gg,f,w,ier)
59          if(ier.ne.0) print*,ier
60          wtotal=0.
61          do 31 i=1,50
62          if(wt(i,it).gt.0.) then
63          wtotal=wtotal+1.
64          end if
65    31    continue
66          rms=sqrt(f/wtotal)
67          do 20 i=1,50
68    20    dev(i)=fr(kex(i),iex(i))-fex(i,it)
69          write (2) it,temp(it),f,rms,ifunct
70          write (2) (x(j),j=1,12)
71          write (2) (i,fex(i,it),dev(i),i=1,50)
72          write (2) (fr(kex(i),iex(i)),wt(i,it),i=1,50)
73          write (2) (kex(i),iex(i),i=1,50)
74    10    continue
75          endfile 2
76          end
77   c
78          subroutine ohn
79   c this subroutine computed fr(k,i) and dfr(k,i,j)=dfr(k,i)/dc(j), j=1,...,9,
80   c and derivative wrto d1,d2,d3 for j=10,11,12.
```

```
81          dimension gam(200,200),lpar(3,8),ng(3)
82         1 ,w(200),z(200,200),fv1(200),fv2(200)
83          common/o/ fr(8,50),dfr(8,50,12)
84         1 ,fex(50,25),kex(400),iex(400),wt(50,25),it
85          common /c/ wtc,c(9),ifunct
86          common /g/ d1,d2,d3, lb(200),mb(200),nb(200),x(12),rho
87          data lpar/1,7,6,2,8,5,3,5,8,4,6,7,5,3,2,6,4,1,7,1,4,8,2,3/
88          data rho,np/7.05,10/
89   c
90          do 93 k=1,8
91   c generate l,m,n tables
92          ig=0
93          do 111 i=1,3
94          do 222 l=1,np+1
95          do 222 m=1,np+1
96          do 222 n=1,np+1
97          if(l+m+n.gt.np+3.or.l+m+n.lt.4) go to 222
98          l2=mod(l-1,2)
99          m2=mod(m-1,2)
100         n2=mod(n-1,2)
101         lmn=4*l2+2*m2+n2+1
102         if(lmn.ne.lpar(i,k)) go to 222
103         ig=ig+1
104         lb(ig)=l-1
105         mb(ig)=m-1
106         nb(ig)=n-1
107   222   continue
108   111   ng(i)=ig
109  c
110  c now the lb,mb,nb tables are filled
111  c next compute gamma, which is the omega-squared matrix.
112  c
113         do 60 ig=1,ng(3)
114         do 60 jg=ig,ng(3)
115         if(ig.le.ng(1)) 11,12
116   11    if(jg.le.ng(1)) 13,14
117   13    gam(ig,jg)=g11(ig,jg)
118         go to 60
119   14    if(jg.le.ng(2)) 4,5
120   4     gam(ig,jg)=g12(ig,jg)
121         go to 60
122   5     gam(ig,jg)=g13(ig,jg)
123         go to 60
124   12    if(ig.le.ng(2)) 10,20
125   10    if(jg.le.ng(2)) 40,50
126   40    gam(ig,jg)=g22(ig,jg)
127         go to 60
128   50    gam(ig,jg)=g23(ig,jg)
129         go to 60
130   20    gam(ig,jg)=g33(ig,jg)
131   60    if(ig.ne.jg) gam(jg,ig)=gam(ig,jg)
132  c
133  c
134  c now the gamma matrix is filled. diagonalize it next.
135         call rs(200,ng(3),gam,w,1,z,fv1,fv2,ierr)
136  c      if(ierr.ne.0) print*,"ierr= ",ierr
137         twopi=2.*acos(-1.)
138         do 91 i=1,ng(3)
139         if(w(i).lt.1.e-6) w(i)=0.
140   91    w(i)=sqrt(w(i))/twopi
141         i0=0
142         if(w(1).eq.0.) i0=1
143         do 99 i=1,50
144   99    if(i+i0.le.ng(3)) fr(k,i)=w(i+i0)
145  c      print*,"k,fr=",k,fr(k,1),fr(k,2),fr(k,3)
```

```
176            if(j.eq.8) gam(ig,jg)=g1(ig,jg)
177            if(j.eq.7) gam(ig,jg)=g2(ig,jg)
178     660    if(ig.ne.jg) gam(jg,ig)=gam(ig,jg)
179            do 697 i=1,min0(ng(3)-i0,50)
180            do 698 l=1,ng(3)
181     698    w(l)=sdot(ng(3),gam(l,1),200,z(1,i+i0),1)
182            dfr(k,i,j)=sdot(ng(3),z(1,i+i0),1,w,1)*.5/
183         1  (twopi**2*fr(k,i))
184 c          if(i.le.2) print*,"k,i,j,dfr= ",k,i,j,dfr(k,i,j)
185     697    continue
186 c
187 c end of do loop on j
188 c
189     699    continue
190 c
191            do 1699 j=10,12
192            do 1660 ig=1,ng(3)
193            do 1660 jg=ig,ng(3)
194            gam(ig,jg)=0.
195            if(ig.le.ng(1)) 1611,1612
196    1611    if(jg.le.ng(1)) 1613,1614
197    1613    if(j.eq.10) gam(ig,jg)=-2.*c(1)*g1(ig,jg)/x(10)
198            if(j.eq.11) gam(ig,jg)=-2.*c(9)*g2(ig,jg)/x(11)
199            if(j.eq.12) gam(ig,jg)=-2.*c(8)*g3(ig,jg)/x(12)
200            go to 1660
201    1614    if(jg.le.ng(2)) 1604,1605
202    1604    if(j.eq.10) gam(ig,jg)=-(c(9)*g8(ig,jg)+c(6)*g9(ig,jg))/x(10)
203            if(j.eq.11) gam(ig,jg)=-(c(9)*g8(ig,jg)+c(6)*g9(ig,jg))/x(11)
204            go to 1660
205    1605    if(j.eq.10) gam(ig,jg)=-(c(8)*g7(ig,jg)+c(5)*g6(ig,jg))/x(10)
206            if(j.eq.12) gam(ig,jg)=-(c(8)*g7(ig,jg)+c(5)*g6(ig,jg))/x(12)
207            go to 1660
208    1612    if(ig.le.ng(2))1610,1620
209    1610    if(jg.le.ng(2))1640,1650
210    1640    if(j.eq.10) gam(ig,jg)=-2.*c(9)*g1(ig,jg)/x(10)
211            if(j.eq.11) gam(ig,jg)=-2.*c(2)*g2(ig,jg)/x(11)
212            if(j.eq.12) gam(ig,jg)=-2.*c(7)*g3(ig,jg)/x(12)
213            go to 1660
214    1650    if(j.eq.11) gam(ig,jg)=-(c(7)*g4(ig,jg)+c(4)*g5(ig,jg))/x(11)
215            if(j.eq.12) gam(ig,jg)=-(c(7)*g4(ig,jg)+c(4)*g5(ig,jg))/x(12)
216            go to 1660
217    1620    if(j.eq.10) gam(ig,jg)=-2.*c(8)*g1(ig,jg)/x(10)
218            if(j.eq.11) gam(ig,jg)=-2.*c(7)*g2(ig,jg)/x(11)
219            if(j.eq.12) gam(ig,jg)=-2.*c(3)*g3(ig,jg)/x(12)
220    1660    if(ig.ne.jg) gam(jg,ig)=gam(ig,jg)
221            do 1697 i=1,min0(ng(3)-i0,50)
222            do 1698 l=1,ng(3)
223    1698    w(l)=sdot(ng(3),gam(l,1),200,z(1,i+i0),1)
224            dfr(k,i,j)=sdot(ng(3),z(1,i+i0),1,w,1)*.5/
225         1  (twopi**2*fr(k,i))
226 c          if(i.le.2) print*,"k,i,j,dfr= ",k,i,j,dfr(k,i,j)
227    1697    continue
228 c
229 c end of do loop on j
230 c
231    1699    continue
232 c
233 c end of do loop on k
234 c
235      93    continue
236            return
237            end
238 c
239 c
```

```
240         subroutine funct(n,x,f,gg)
241         common /c/ wtc,c(9),ifunct
242         dimension x(n),gg(n),c0(9),fr1(8,50),fr2(8,50)
243         common/o/ fr(8,50),dfr(8,50,12)
244       1 ,fex(50,25),kex(400),iex(400),wt(50,25),it
245 c this subroutine computes the weighted sum f and its derivative
246 c wrto x(1),x(2),...,x(n), where x is defined in terms of c(1),..c(9),
247 c and x(10),x(11),x(12) are d1,d2,d3.
248         ifunct=ifunct+1
249         print*,"ifunct= ",ifunct
250         do 32 j=1,9
251  32     c(j)=x(j)
252         print*,"elastic constants"
253         print 101,(c(j),j=1,9)
254         print*,"d1,d2,d3"
255         print 101,(x(j),j=10,12)
256 101     format(6g12.5)
257 c
258         call ohn
259         do 10 l=1,400
260         fr1(l)=fr(l)
261         fr2(l)=fr(l)
262         kex(l)=mod(l-1,8)+1
263  10     iex(l)=(l+7)/8
264         call ssort(fr1,kex,400,2)
265         call ssort(fr2,iex,400,2)
266         f=0.
267         do 3 j=1,n
268   3     gg(j)=0.
269         do 1 i=1,50
270         if(wt(i,it).gt.0.) then
271         dif=fex(i,it)-fr(kex(i),iex(i))
272         print*,"i,fex,dif= ",i,fex(i,it),dif
273         dif2=dif**2
274         wt2=wt(i,it)**2
275         flor=dif2/(1.+dif2/wt2)
276         f=f+flor
277         do 2 j=1,n
278   2     gg(j)=gg(j)-2.*dif*dfr(kex(i),iex(i),j)*(wt2/(wt2+dif2))**2
279         end if
280   1     continue
281         print*,"f,gg(1),gg(2)= ",f,gg(1),gg(2)
282         return
283         end
284 c
285 c
286         function g1(ig,jg)
287         common /g/ d1,d2,d3, lb(200),mb(200),nb(200),x(12),rho
288         g1=0.
289         if(mb(ig).eq.mb(jg).and.nb(ig).eq.nb(jg).and.
290       1 mod(lb(ig)+lb(jg),2).eq.0) 1,2
291   1     fll=min0(lb(ig),lb(jg))
292         g1=.5*fll*(fll+1.)*sqrt(float((2*lb(ig)+1)*(2*lb(jg)+1)))
293       1 /(rho*x(10)**2)
294   2     return
295         end
296 c
297 c
298         function g2(ig,jg)
299         common /g/ d1,d2,d3, lb(200),mb(200),nb(200),x(12),rho
300         g2=0.
301         if(lb(ig).eq.lb(jg).and.nb(ig).eq.nb(jg).and.
302       1 mod(mb(ig)+mb(jg),2).eq.0) 1,2
303   1     fll=min0(mb(ig),mb(jg))
304         g2=.5*fll*(fll+1.)*sqrt(float((2*mb(ig)+1)*(2*mb(jg)+1)))
```

```
305         1 /(rho*x(11)**2)
306   2     return
307         end
308 c
309 c
310         function g3(ig,jg)
311         common /g/ d1,d2,d3, lb(200),mb(200),nb(200),x(12),rho
312         g3=0.
313         if(mb(ig).eq.mb(jg).and.lb(ig).eq.lb(jg).and.
314       1 mod(nb(ig)+nb(jg),2).eq.0) 1,2
315   1     fll=min0(nb(ig),nb(jg))
316         g3=.5*fll*(fll+1.)*sqrt(float((2*nb(ig)+1)*(2*nb(jg)+1)))
317       1 /(rho*x(12)**2)
318   2     return
319         end
320 c
321 c
322         function g4(ig,jg)
323         common /g/ d1,d2,d3, lb(200),mb(200),nb(200),x(12),rho
324         g4=0.
325         if(lb(ig).eq.lb(jg).and.mb(ig).lt.mb(jg).and.nb(ig).gt.nb(jg)) 1,2
326   1     if(mod(nb(ig)+nb(jg),2)*mod(mb(ig)+mb(jg),2).eq.0) go to 2
327         g4=sqrt(float((2*mb(ig)+1)*(2*mb(jg)+1)*(2*nb(ig)
328       1 +1)*(2*nb(jg)+1)))/(rho*x(11)*x(12))
329   2     return
330         end
331 c
332 c
333         function g5(ig,jg)
334         common /g/ d1,d2,d3, lb(200),mb(200),nb(200),x(12),rho
335         g5=0.
336         if(lb(ig).eq.lb(jg).and.nb(ig).lt.nb(jg).and.mb(ig).gt.mb(jg)) 1,2
337   1     if(mod(nb(ig)+nb(jg),2)*mod(mb(ig)+mb(jg),2).eq.0) go to 2
338         g5=sqrt(float((2*mb(ig)+1)*(2*mb(jg)+1)*(2*nb(ig)
339       1 +1)*(2*nb(jg)+1)))/(rho*x(11)*x(12))
340   2     return
341         end
342 c
343 c
344         function g6(ig,jg)
345         common /g/ d1,d2,d3, lb(200),mb(200),nb(200),x(12),rho
346         g6=0.
347         if(mb(ig).eq.mb(jg).and.nb(ig).lt.nb(jg).and.lb(ig).gt.lb(jg)) 1,2
348   1     if(mod(lb(ig)+lb(jg),2)*mod(nb(ig)+nb(jg),2).eq.0) go to 2
349         g6=sqrt(float((2*lb(ig)+1)*(2*lb(jg)+1)*(2*nb(ig)
350       1 +1)*(2*nb(jg)+1)))/(rho*x(10)*x(12))
351   2     return
352         end
353 c
354 c
355         function g7(ig,jg)
356         common /g/ d1,d2,d3, lb(200),mb(200),nb(200),x(12),rho
357         g7=0.
358         if(mb(ig).eq.mb(jg).and.lb(ig).lt.lb(jg).and.nb(ig).gt.nb(jg)) 1,2
359   1     if(mod(lb(ig)+lb(jg),2)*mod(nb(ig)+nb(jg),2).eq.0) go to 2
360         g7=sqrt(float((2*lb(ig)+1)*(2*lb(jg)+1)*(2*nb(ig)
361       1 +1)*(2*nb(jg)+1)))/(rho*x(10)*x(12))
362   2     return
363         end
364 c
365 c
366         function g8(ig,jg)
367         common /g/ d1,d2,d3, lb(200),mb(200),nb(200),x(12),rho
368         g8=0.
369         if(nb(ig).eq.nb(jg).and.lb(ig).lt.lb(jg).and.mb(ig).gt.mb(jg)) 1,2
370   1     if(mod(lb(ig)+lb(jg),2)*mod(mb(ig)+mb(jg),2).eq.0) go to 2
```

```
371         g8=sqrt(float((2*mb(ig)+1)*(2*mb(jg)+1)*(2*lb(ig)
372       1 +1)*(2*lb(jg)+1)))/(rho*x(10)*x(11))
373   2   return
374       end
375 c
376 c
377       function g9(ig,jg)
378       common /g/ d1,d2,d3, lb(200),mb(200),nb(200),x(12),rho
379       g9=0.
380       if(nb(ig).eq.nb(jg).and.lb(ig).gt.lb(jg).and.mb(ig).lt.mb(jg)) 1,2
381   1   if(mod(lb(ig)+lb(jg),2)*mod(mb(ig)+mb(jg),2).eq.0) go to 2
382       g9=sqrt(float((2*mb(ig)+1)*(2*mb(jg)+1)*(2*lb(ig)
383       1 +1)*(2*lb(jg)+1)))/(rho*x(10)*x(11))
384   2   return
385       end
386 c
387 c
388       function g11(ig,jg)
389       common /c/ wtc,c(9),ifunct
390       g11=c(1)*g1(ig,jg)+c(9)*g2(ig,jg)+c(8)*g3(ig,jg)
391       return
392       end
393 c
394 c
395       function g22(ig,jg)
396       common /c/ wtc,c(9),ifunct
397       g22=c(9)*g1(ig,jg)+c(2)*g2(ig,jg)+c(7)*g3(ig,jg)
398       return
399       end
400 c
401 c
402       function g33(ig,jg)
403       common /c/ wtc,c(9),ifunct
404       g33=c(8)*g1(ig,jg)+c(7)*g2(ig,jg)+c(3)*g3(ig,jg)
405       return
406       end
407 c
408 c
409       function g12(ig,jg)
410       common /c/ wtc,c(9),ifunct
411       g12=c(9)*g8(ig,jg)+c(6)*g9(ig,jg)
412       return
413       end
414 c
415 c
416       function g13(ig,jg)
417       common /c/ wtc,c(9),ifunct
418       g13=c(8)*g7(ig,jg)+c(5)*g6(ig,jg)
419       return
420       end
421 c
422 c
423       function g23(ig,jg)
424       common /c/ wtc,c(9),ifunct
425       g23=c(7)*g4(ig,jg)+c(4)*g5(ig,jg)
426       return
427       end
*t*
1         SUBROUTINE RS(NM,N,A,W,MATZ,Z,FV1,FV2,IERR)
2 C
3         INTEGER N,NM,IERR,MATZ
4         REAL A(NM,N),W(N),Z(NM,N),FV1(N),FV2(N)
5 C
```

```
 6   C***FIRST EXECUTABLE STATEMENT   RS
 7         IF (N .LE. NM) GO TO 10
 8         IERR = 10 * N
 9         GO TO 50
10   C
11      10 IF (MATZ .NE. 0) GO TO 20
12   C     .......... FIND EIGENVALUES ONLY ..........
13         CALL  TRED1(NM,N,A,W,FV1,FV2)
14         CALL  TQLRAT(N,W,FV2,IERR)
15         GO TO 50
16   C     .......... FIND BOTH EIGENVALUES AND EIGENVECTORS ..........
17      20 CALL  TRED2(NM,N,A,W,FV1,Z)
18         CALL  TQL2(NM,N,W,FV1,Z,IERR)
19      50 RETURN
20         END
21         SUBROUTINE SSORT(X,Y,N,KFLAG)
22         DIMENSION X(N),Y(N),IL(21),IU(21)
23   C***FIRST EXECUTABLE STATEMENT   SSORT
24         NN = N
25         IF (NN.GE.1) GO TO 10
26         CALL XERROR ( 'SSORT- THE NUMBER OF VALUES TO BE SORTED WAS NOT PO
27        1SITIVE.',58,1,1)
28         RETURN
29      10 KK = IABS(KFLAG)
30         IF ((KK.EQ.1).OR.(KK.EQ.2)) GO TO 15
31         CALL XERROR ( 'SSORT- THE SORT CONTROL PARAMETER, K, WAS NOT 2, 1,
32        1 -1, OR -2.',62,2,1)
33         RETURN
34   C
35   C ALTER ARRAY X TO GET DECREASING ORDER IF NEEDED
36   C
37      15 IF (KFLAG.GE.1) GO TO 30
38         DO 20 I=1,NN
39      20 X(I) = -X(I)
40      30 GO TO (100,200),KK
41   C
42   C SORT X ONLY
43   C
44     100 CONTINUE
45         M=1
46         I=1
47         J=NN
48         R=.375
49     110 IF (I .EQ. J) GO TO 155
50     115 IF (R .GT. .5898437) GO TO 120
51         R=R+3.90625E-2
52         GO TO 125
53     120 R=R-.21875
54     125 K=I
55   C                                     SELECT A CENTRAL ELEMENT OF THE
56   C                                     ARRAY AND SAVE IT IN LOCATION T
57         IJ = I + IFIX (FLOAT (J-I) * R)
58         T=X(IJ)
59   C                                     IF FIRST ELEMENT OF ARRAY IS GREATER
60   C                                     THAN T, INTERCHANGE WITH T
61         IF (X(I) .LE. T) GO TO 130
62         X(IJ)=X(I)
63         X(I)=T
64         T=X(IJ)
65     130 L=J
66   C                                     IF LAST ELEMENT OF ARRAY IS LESS THAN
67   C                                     T, INTERCHANGE WITH T
68         IF (X(J) .GE. T) GO TO 140
```

```
 69           X(IJ)=X(J)
 70           X(J)=T
 71           T=X(IJ)
 72 C                              IF FIRST ELEMENT OF ARRAY IS GREATER
 73 C                              THAN T, INTERCHANGE WITH T
 74           IF (X(I) .LE. T) GO TO 140
 75           X(IJ)=X(I)
 76           X(I)=T
 77           T=X(IJ)
 78           GO TO 140
 79    135  TT=X(L)
 80           X(L)=X(K)
 81           X(K)=TT
 82 C                              FIND AN ELEMENT IN THE SECOND HALF OF
 83 C                              THE ARRAY WHICH IS SMALLER THAN T
 84    140  L=L-1
 85           IF (X(L) .GT. T) GO TO 140
 86 C                              FIND AN ELEMENT IN THE FIRST HALF OF
 87 C                              THE ARRAY WHICH IS GREATER THAN T
 88    145  K=K+1
 89           IF (X(K) .LT. T) GO TO 145
 90 C                              INTERCHANGE THESE ELEMENTS
 91           IF (K .LE. L) GO TO 135
 92 C                              SAVE UPPER AND LOWER SUBSCRIPTS OF
 93 C                              THE ARRAY YET TO BE SORTED
 94           IF (L-I .LE. J-K) GO TO 150
 95           IL(M)=I
 96           IU(M)=L
 97           I=K
 98           M=M+1
 99           GO TO 160
100    150  IL(M)=K
101           IU(M)=J
102           J=L
103           M=M+1
104           GO TO 160
105 C
106 C                              BEGIN AGAIN ON ANOTHER PORTION OF
107    155  M=M-1                  THE UNSORTED ARRAY
108           IF (M .EQ. 0) GO TO 300
109           I=IL(M)
110           J=IU(M)
111    160  IF (J-I .GE. 1) GO TO 125
112           IF (I .EQ. 1) GO TO 110
113           I=I-1
114    165  I=I+1
115           IF (I .EQ. J) GO TO 155
116           T=X(I+1)
117           IF (X(I) .LE. T) GO TO 165
118           K=I
119    170  X(K+1)=X(K)
120           K=K-1
121           IF (T .LT. X(K)) GO TO 170
122           X(K+1)=T
123           GO TO 165
124 C
125 C SORT X AND CARRY Y ALONG
126 C
127    200  CONTINUE
128           M=1
129           I=1
130           J=NN
131           R=.375
132    210  IF (I .EQ. J) GO TO 255
```

```
133    215 IF (R .GT. .5898437) GO TO 220
134        R=R+3.90625E-2
135        GO TO 225
136    220 R=R-.21875
137    225 K=I
138 C                                              SELECT A CENTRAL ELEMENT OF THE
139 C                                              ARRAY AND SAVE IT IN LOCATION T
140        IJ = I + IFIX (FLOAT (J-I) *R)
141        T=X(IJ)
142        TY= Y(IJ)
143 C                                              IF FIRST ELEMENT OF ARRAY IS GREATER
144 C                                              THAN T, INTERCHANGE WITH T
145        IF (X(I) .LE. T) GO TO 230
146        X(IJ)=X(I)
147        X(I)=T
148        T=X(IJ)
149        Y(IJ)= Y(I)
150        Y(I)=TY
151        TY= Y(IJ)
152    230 L=J
153 C                                              IF LAST ELEMENT OF ARRAY IS LESS THAN
154 C                                              T, INTERCHANGE WITH T
155        IF (X(J) .GE. T) GO TO 240
156        X(IJ)=X(J)
157        X(J)=T
158        T=X(IJ)
159        Y(IJ)= Y(J)
160        Y(J)=TY
161        TY= Y(IJ)
162 C                                              IF FIRST ELEMENT OF ARRAY IS GREATER
163 C                                              THAN T, INTERCHANGE WITH T
164        IF (X(I) .LE. T) GO TO 240
165        X(IJ)=X(I)
166        X(I)=T
167        T=X(IJ)
168        Y(IJ)= Y(I)
169        Y(I)=TY
170        TY= Y(IJ)
171        GO TO 240
172    235 TT=X(L)
173        X(L)=X(K)
174        X(K)=TT
175        TTY= Y(L)
176        Y(L)= Y(K)
177        Y(K)=TTY
178 C                                              FIND AN ELEMENT IN THE SECOND HALF OF
179 C                                              THE ARRAY WHICH IS SMALLER THAN T
180    240 L=L-1
181        IF (X(L) .GT. T) GO TO 240
182 C                                              FIND AN ELEMENT IN THE FIRST HALF OF
183 C                                              THE ARRAY WHICH IS GREATER THAN T
184    245 K=K+1
185        IF (X(K) .LT. T) GO TO 245
186 C                                              INTERCHANGE THESE ELEMENTS
187        IF (K .LE. L) GO TO 235
188 C                                              SAVE UPPER AND LOWER SUBSCRIPTS OF
189 C                                              THE ARRAY YET TO BE SORTED
190        IF (L-I .LE. J-K) GO TO 250
191        IL(M)=I
192        IU(M)=L
193        I=K
194        M=M+1
195        GO TO 260
196    250 IL(M)=K
197        IU(M)=J
```

```
198            J=L
199            M=M+1
200            GO TO 260                      BEGIN AGAIN ON ANOTHER PORTION OF
201    C                                      THE UNSORTED ARRAY
202    C
203      255   M=M-1
204            IF (M .EQ. 0) GO TO 300
205            I=IL(M)
206            J=IU(M)
207      260   IF (J-I .GE. 1) GO TO 225
208            IF (I .EQ. 1) GO TO 210
209            I=I-1
210      265   I=I+1
211            IF (I .EQ. J) GO TO 255
212            T=X(I+1)
213            TY= Y(I+1)
214            IF (X(I) .LE. T) GO TO 265
215            K=I
216      270   X(K+1)=X(K)
217            Y(K+1)= Y(K)
218            K=K-1
219            IF (T .LT. X(K)) GO TO 270
220            X(K+1)=T
221            Y(K+1)=TY
222            GO TO 265
223    C
224    C CLEAN UP
225    C
226      300   IF (KFLAG.GE.1) RETURN
227            DO 310 I=1,NN
228      310   X(I) = -X(I)
229            RETURN
230            END
231            REAL FUNCTION SDOT(N,SX,INCX,SY,INCY)
232    C
233            REAL SX(1),SY(1)
234    C***FIRST EXECUTABLE STATEMENT  SDOT
235            SDOT = 0.0E0
236            IF(N.LE.0)RETURN
237            IF(INCX.EQ.INCY) IF(INCX-1)5,20,60
238        5 CONTINUE
239    C
240    C         CODE FOR UNEQUAL INCREMENTS OR NONPOSITIVE INCREMENTS.
241    C
242            IX = 1
243            IY = 1
244            IF(INCX.LT.0)IX = (-N+1)*INCX + 1
245            IF(INCY.LT.0)IY = (-N+1)*INCY + 1
246            DO 10 I = 1,N
247              SDOT = SDOT + SX(IX)*SY(IY)
248              IX = IX + INCX
249              IY = IY + INCY
250       10 CONTINUE
251            RETURN
252    C
253    C         CODE FOR BOTH INCREMENTS EQUAL TO 1
254    C
255    C
256    C         CLEAN-UP LOOP SO REMAINING VECTOR LENGTH IS A MULTIPLE OF 5.
257    C
258       20 M = MOD(N,5)
259            IF( M .EQ. 0 ) GO TO 40
260            DO 30 I = 1,M
261              SDOT = SDOT + SX(I)*SY(I)
```

```
262      30 CONTINUE
263         IF( N .LT. 5 ) RETURN
264      40 MP1 = M + 1
265         DO 50 I = MP1,N,5
266            SDOT = SDOT + SX(I)*SY(I) + SX(I + 1)*SY(I + 1) +
267       1    SX(I + 2)*SY(I + 2) + SX(I + 3)*SY(I + 3) + SX(I + 4)*SY(I + 4)
268      50 CONTINUE
269         RETURN
270 C
271 C        CODE FOR POSITIVE EQUAL INCREMENTS .NE.1.
272 C
273      60 CONTINUE
274         NS=N*INCX
275         DO 70 I=1,NS,INCX
276            SDOT = SDOT + SX(I)*SY(I)
277      70   CONTINUE
278         RETURN
279         END
```

```
*t*
  1         SUBROUTINE TQL2(NM,N,D,E,Z,IERR)
  2 C
  3         INTEGER I,J,K,L,M,N,II,L1,L2,NM,MML,IERR
  4         REAL D(N),E(N),Z(NM,N)
  5         REAL B,C,C2,C3,DL1,EL1,F,G,H,P,R,S,S2
  6         REAL PYTHAG
  7 C
  8 C***FIRST EXECUTABLE STATEMENT   TQL2
  9         IERR = 0
 10         IF (N .EQ. 1) GO TO 1001
 11 C
 12         DO 100 I = 2, N
 13     100 E(I-1) = E(I)
 14 C
 15         F = 0.0E0
 16         B = 0.0E0
 17         E(N) = 0.0E0
 18 C
 19         DO 240 L = 1, N
 20            J = 0
 21            H = ABS(D(L)) + ABS(E(L))
 22            IF (B .LT. H) B = H
 23 C     .......... LOOK FOR SMALL SUB-DIAGONAL ELEMENT ..........
 24            DO 110 M = L, N
 25               IF (B + ABS(E(M)) .EQ. B) GO TO 120
 26 C     .......... E(N) IS ALWAYS ZERO, SO THERE IS NO EXIT
 27 C                THROUGH THE BOTTOM OF THE LOOP ..........
 28     110    CONTINUE
 29 C
 30     120    IF (M .EQ. L) GO TO 220
 31     130    IF (J .EQ. 30) GO TO 1000
 32            J = J + 1
 33 C     .......... FORM SHIFT ..........
 34            L1 = L + 1
 35            L2 = L1 + 1
 36            G = D(L)
 37            P = (D(L1) - G) / (2.0E0 * E(L))
 38            R = PYTHAG(P,1.0E0)
 39            D(L) = E(L) / (P + SIGN(R,P))
 40            D(L1) = E(L) * (P + SIGN(R,P))
 41            DL1 = D(L1)
 42            H = G - D(L)
 43            IF (L2 .GT. N) GO TO 145
 44 C
```

```
45              DO 140 I = L2, N
46    140       D(I) = D(I) - H
47  C
48    145    F = F + H
49  C   .......... QL TRANSFORMATION ..........
50           P = D(M)
51           C = 1.0E0
52           C2 = C
53           EL1 = E(L1)
54           S = 0.0E0
55           MML = M - L
56  C   .......... FOR I=M-1 STEP -1 UNTIL L DO -- ..........
57           DO 200 II = 1, MML
58              C3 = C2
59              C2 = C
60              S2 = S
61              I = M - II
62              G = C * E(I)
63              H = C * P
64              IF (ABS(P) .LT. ABS(E(I))) GO TO 150
65              C = E(I) / P
66              R = SQRT(C*C+1.0E0)
67              E(I+1) = S * P * R
68              S = C / R
69              C = 1.0E0 / R
70              GO TO 160
71    150       C = P / E(I)
72              R = SQRT(C*C+1.0E0)
73              E(I+1) = S * E(I) * R
74              S = 1.0E0 / R
75              C = C * S
76    160       P = C * D(I) - S * G
77              D(I+1) = H + S * (C * G + S * D(I))
78  C   .......... FORM VECTOR ..........
79              DO 180 K = 1, N
80                 H = Z(K,I+1)
81                 Z(K,I+1) = S * Z(K,I) + C * H
82                 Z(K,I) = C * Z(K,I) - S * H
83    180       CONTINUE
84  C
85    200    CONTINUE
86  C
87           P = -S * S2 * C3 * EL1 * E(L) / DL1
88           E(L) = S * P
89           D(L) = C * P
90           IF (B + ABS(E(L))) .GT. B) GO TO 130
91    220    D(L) = D(L) + F
92    240 CONTINUE
93  C   .......... ORDER EIGENVALUES AND EIGENVECTORS ..........
94        DO 300 II = 2, N
95           I = II - 1
96           K = I
97           P = D(I)
98  C
99           DO 260 J = II, N
100             IF (D(J) .GE. P) GO TO 260
101             K = J
102             P = D(J)
103    260   CONTINUE
104 C
105          IF (K .EQ. I) GO TO 300
106          D(K) = D(I)
107          D(I) = P
108 C
```

```
109              DO 280 J = 1, N
110                 P = Z(J,I)
111                 Z(J,I) = Z(J,K)
112                 Z(J,K) = P
113      280     CONTINUE
114 C
115      300 CONTINUE
116 C
117              GO TO 1001
118 C         .......... SET ERROR -- NO CONVERGENCE TO AN
119 C                    EIGENVALUE AFTER 30 ITERATIONS ..........
120     1000 IERR = L
121     1001 RETURN
122              END
123              SUBROUTINE TQLRAT(N,D,E2,IERR)
124 C
125              INTEGER I,J,L,M,N,II,L1,MML,IERR
126              REAL D(N),E2(N)
127              REAL B,C,F,G,H,P,R,S,MACHEP
128              REAL PYTHAG
129 C
130              SAVE MACHEP
131              DATA MACHEP/1.0E0/
132 C***FIRST EXECUTABLE STATEMENT  TQLRAT
133              IF (MACHEP .NE. 1.0E0) GO TO 10
134       05 MACHEP = 0.5E0*MACHEP
135              IF (1.0E0 + MACHEP .GT. 1.0E0) GO TO 05
136              MACHEP = 2.0E0*MACHEP
137 C
138       10 IERR = 0
139              IF (N .EQ. 1) GO TO 1001
140 C
141              DO 100 I = 2, N
142      100 E2(I-1) = E2(I)
143 C
144              F = 0.0E0
145              B = 0.0E0
146              E2(N) = 0.0E0
147 C
148              DO 290 L = 1, N
149                 J = 0
150                 H = MACHEP * (ABS(D(L)) + SQRT(E2(L)))
151                 IF (B .GT. H) GO TO 105
152                 B = H
153                 C = B * B
154 C         .......... LOOK FOR SMALL SQUARED SUB-DIAGONAL ELEMENT ..........
155      105    DO 110 M = L, N
156                   IF (E2(M) .LE. C) GO TO 120
157 C         .......... E2(N) IS ALWAYS ZERO, SO THERE IS NO EXIT
158 C                    THROUGH THE BOTTOM OF THE LOOP ..........
159      110    CONTINUE
160 C
161      120    IF (M .EQ. L) GO TO 210
162      130    IF (J .EQ. 30) GO TO 1000
163                 J = J + 1
164 C         .......... FORM SHIFT ..........
165                 L1 = L + 1
166                 S = SQRT(E2(L))
167                 G = D(L)
168                 P = (D(L1) - G) / (2.0E0 * S)
169                 R = PYTHAG(P,1.0E0)
170                 D(L) = S / (P + SIGN(R,P))
171                 H = G - D(L)
172 C
173                 DO 140 I = L1, N
```

```
174  140      D(I) = D(I) - H
175 C
176          F = F + H
177 C   .......... RATIONAL QL TRANSFORMATION ..........
178          G = D(M)
179          IF (G .EQ. 0.0E0) G = B
180          H = G
181          S = 0.0E0
182          MML = M - L
183 C   .......... FOR I=M-1 STEP -1 UNTIL L DO -- ..........
184          DO 200 II = 1, MML
185             I = M - II
186             P = G * H
187             R = P + E2(I)
188             E2(I+1) = S * R
189             S = E2(I) / R
190             D(I+1) = H + S * (H + D(I))
191             G = D(I) - E2(I) / G
192             IF (G .EQ. 0.0E0) G = B
193             H = G * P / R
194  200     CONTINUE
195 C
196          E2(L) = S * G
197          D(L) = H
198 C   .......... GUARD AGAINST UNDERFLOW IN CONVERGENCE TEST ..........
199          IF (H .EQ. 0.0E0) GO TO 210
200          IF (ABS(E2(L)) .LE. ABS(C/H)) GO TO 210
201          E2(L) = H * E2(L)
202          IF (E2(L) .NE. 0.0E0) GO TO 130
203  210     P = D(L) + F
204 C   .......... ORDER EIGENVALUES ..........
205          IF (L .EQ. 1) GO TO 250
206 C   .......... FOR I=L STEP -1 UNTIL 2 DO -- ..........
207          DO 230 II = 2, L
208             I = L + 2 - II
209             IF (P .GE. D(I-1)) GO TO 270
210             D(I) = D(I-1)
211  230     CONTINUE
212 C
213  250     I = 1
214  270     D(I) = P
215  290 CONTINUE
216 C
217          GO TO 1001
218 C   .......... SET ERROR -- NO CONVERGENCE TO AN
219 C              EIGENVALUE AFTER 30 ITERATIONS ..........
220  1000 IERR = L
221  1001 RETURN
222       END
223       SUBROUTINE TRED1(NM,N,A,D,E,E2)
224 C
225       INTEGER I,J,K,L,N,II,NM,JP1
226       REAL A(NM,N),D(N),E(N),E2(N)
227       REAL F,G,H,SCALE
228 C
229 C***FIRST EXECUTABLE STATEMENT  TRED1
230       DO 100 I = 1, N
231  100 D(I) = A(I,I)
232 C   .......... FOR I=N STEP -1 UNTIL 1 DO -- ..........
233       DO 300 II = 1, N
234          I = N + 1 - II
235          L = I - 1
236          H = 0.0E0
```

```
237             SCALE = 0.0E0
238             IF (L .LT. 1) GO TO 130
239 C     .......... SCALE ROW (ALGOL TOL THEN NOT NEEDED) ..........
240             DO 120 K = 1, L
241  120        SCALE = SCALE + ABS(A(I,K))
242 C
243             IF (SCALE .NE. 0.0E0) GO TO 140
244  130        E(I) = 0.0E0
245             E2(I) = 0.0E0
246             GO TO 290
247 C
248  140        DO 150 K = 1, L
249               A(I,K) = A(I,K) / SCALE
250               H = H + A(I,K) * A(I,K)
251  150        CONTINUE
252 C
253             E2(I) = SCALE * SCALE * H
254             F = A(I,L)
255             G = -SIGN(SQRT(H),F)
256             E(I) = SCALE * G
257             H = H - F * G
258             A(I,L) = F - G
259             IF (L .EQ. 1) GO TO 270
260             F = 0.0E0
261 C
262             DO 240 J = 1, L
263               G = 0.0E0
264 C     .......... FORM ELEMENT OF A*U ..........
265               DO 180 K = 1, J
266  180          G = G + A(J,K) * A(I,K)
267 C
268               JP1 = J + 1
269               IF (L .LT. JP1) GO TO 220
270 C
271               DO 200 K = JP1, L
272  200          G = G + A(K,J) * A(I,K)
273 C     .......... FORM ELEMENT OF P ..........
274  220          E(J) = G / H
275               F = F + E(J) * A(I,J)
276  240        CONTINUE
277 C
278             H = F / (H + H)
279 C     .......... FORM REDUCED A ..........
280             DO 260 J = 1, L
281               F = A(I,J)
282               G = E(J) - H * F
283               E(J) = G
284 C
285               DO 260 K = 1, J
286                 A(J,K) = A(J,K) - F * E(K) - G * A(I,K)
287  260        CONTINUE
288 C
289  270        DO 280 K = 1, L
290  280        A(I,K) = SCALE * A(I,K)
291 C
292  290        H = D(I)
293             D(I) = A(I,I)
294             A(I,I) = H
295  300  CONTINUE
296 C
297       RETURN
298       END
299       SUBROUTINE TRED2(NM,N,A,D,E,Z)
300 C
```

```
301         INTEGER I,J,K,L,N,II,NM,JP1
302         REAL A(NM,N),D(N),E(N),Z(NM,N)
303         REAL F,G,H,HH,SCALE
304   C
305   C***FIRST EXECUTABLE STATEMENT  TRED2
306         DO 100 I = 1, N
307   C
308            DO 100 J = 1, I
309               Z(I,J) = A(I,J)
310   100  CONTINUE
311   C
312         IF (N .EQ. 1) GO TO 320
313   C     .......... FOR I=N STEP -1 UNTIL 2 DO -- ..........
314         DO 300 II = 2, N
315            I = N + 2 - II
316            L = I - 1
317            H = 0.0E0
318            SCALE = 0.0E0
319            IF (L .LT. 2) GO TO 130
320   C     .......... SCALE ROW (ALGOL TOL THEN NOT NEEDED) ..........
321            DO 120 K = 1, L
322   120        SCALE = SCALE + ABS(Z(I,K))
323   C
324            IF (SCALE .NE. 0.0E0) GO TO 140
325   130     E(I) = Z(I,L)
326            GO TO 290
327   C
328   140     DO 150 K = 1, L
329               Z(I,K) = Z(I,K) / SCALE
330               H = H + Z(I,K) * Z(I,K)
331   150     CONTINUE
332   C
333            F = Z(I,L)
334            G = -SIGN(SQRT(H),F)
335            E(I) = SCALE * G
336            H = H - F * G
337            Z(I,L) = F - G
338            F = 0.0E0
339   C
340            DO 240 J = 1, L
341               Z(J,I) = Z(I,J) / H
342               G = 0.0E0
343   C     .......... FORM ELEMENT OF A*U ..........
344               DO 180 K = 1, J
345   180           G = G + Z(J,K) * Z(I,K)
346   C
347               JP1 = J + 1
348               IF (L .LT. JP1) GO TO 220
349   C
350               DO 200 K = JP1, L
351   200           G = G + Z(K,J) * Z(I,K)
352   C     .......... FORM ELEMENT OF P ..........
353   220        E(J) = G / H
354               F = F + E(J) * Z(I,J)
355   240     CONTINUE
356   C
357            HH = F / (H + H)
358   C     .......... FORM REDUCED A ..........
359            DO 260 J = 1, L
360               F = Z(I,J)
361               G = E(J) - HH * F
362               E(J) = G
363   C
364               DO 260 K = 1, J
```

```
365              Z(J,K) = Z(J,K) - F * E(K) - G * Z(I,K)
366   260    CONTINUE
367 C
368   290    D(I) = H
369   300 CONTINUE
370 C
371   320 D(1) = 0.0E0
372       E(1) = 0.0E0
373 C  .......... ACCUMULATION OF TRANSFORMATION MATRICES ..........
374       DO 500 I = 1, N
375          L = I - 1
376          IF (D(I) .EQ. 0.0E0) GO TO 380
377 C
378          DO 360 J = 1, L
379             G = 0.0E0
380 C
381             DO 340 K = 1, L
382   340       G = G + Z(I,K) * Z(K,J)
383 C
384             DO 360 K = 1, L
385                Z(K,J) = Z(K,J) - G * Z(K,I)
386   360    CONTINUE
387 C
388   380    D(I) = Z(I,I)
389          Z(I,I) = 1.0E0
390          IF (L .LT. 1) GO TO 500
391 C
392          DO 400 J = 1, L
393             Z(I,J) = 0.0E0
394             Z(J,I) = 0.0E0
395   400    CONTINUE
396 C
397   500 CONTINUE
398 C
399       RETURN
400       END
```

```
1       REAL FUNCTION PYTHAG(A,B)
2       REAL A,B
3 C
4       REAL P,Q,R,S,T
5 C***FIRST EXECUTABLE STATEMENT  PYTHAG
6       P = AMAX1(ABS(A),ABS(B))
7       Q = AMIN1(ABS(A),ABS(B))
8       IF (Q .EQ. 0.0E0) GO TO 20
9   10 CONTINUE
10      R = (Q/P)**2
11      T = 4.0E0 + R
12      IF (T .EQ. 4.0E0) GO TO 20
13      S = R/T
14      P = P + 2.0E0*P*S
15      Q = Q*S
16      GO TO 10
17   20 PYTHAG = P
18      RETURN
19      END
```

```
103402        subroutine zxcgr    (funct,n,acc,maxfn,dfpred,x,g,f,w,ier)
103403 c                                specifications for arguments
103404        integer             n,maxfn,ier
103405        real                acc,dfpred,x(n),g(n),f,w(1)
103406 c                                specifications for local variables
103407        integer             maxlin,mxfcon,i,iginit,igopt,iretry,irsdg,
103408      1                     irsdx,iterc,iterfm,iterrs,ixopt,ncalls,nfbeg,
103409      2                     nfopt
103410        real                beta,ddspln,dfpr,fch,finit,fmin,gamden,gama,
103411      1                     ginit,gmin,gnew,gspln,gsqrd,sbound,step,stepch,
103412      2                     stmin,sum,work
103413        data                maxlin/5/,mxfcon/2/
103414 c                                first executable statement
103415        ier = 0
103416 c                                the working space array is split
103417 c                                  into six vectors of length n. the
103418 c                                  first part is used for the search
103419 c                                  direction of an iteration. the
103420 c                                  second and third parts contain the
103421 c                                  information that is required by
103422 c                                  the conjugacy conditions of the
103423 c                                  restart procedure. the fourth part
103424 c                                  contains the gradient at the start
103425 c                                  of an iteration. the fifth part
103426 c                                  contains the parameters that give
103427 c                                  the least calculated value of f.
103428 c                                  the sixth part contains the
103429 c                                  gradient vector where f is least.
103430        irsdx = n
103431        irsdg = irsdx+n
103432        iginit = irsdg+n
103433        ixopt = iginit+n
103434        igopt = ixopt+n
103435 c                                set some parameters to begin the
103436 c                                  calculation. iterc and
103437 c                                  ncalls count the number of
103438 c                                  iterations and calls of funct.
103439 c                                  iterfm is the number of the most
103440 c                                  recent iteration that decreases f.
103441        iterc = 0
103442        ncalls = 0
103443        iterfm = iterc
103444 c                                call subroutine funct. let the
103445 c                                  initial search direction be minus
103446 c                                  the gradient vector. usually the
103447 c                                  parameter iterrs gives the
103448 c                                  iteration number of the most
103449 c                                  recent restart, but it is set to
103450 c                                  zero when the steepest descent
103451 c                                  direction is used.
103452      5 ncalls = ncalls+1
103453        call funct (n,x,f,g)
103454        if (ncalls.ge.2) go to 20
103455     10 do 15 i=1,n
103456     15 w(i) = -g(i)
103457        iterrs = 0
103458        if (iterc.gt.0) go to 80
103459 c                                set sum to g squared. gmin and gnew
103460 c                                  are the old and the new
103461 c                                  directional derivatives along the
103462 c                                  current search direction. let fch
103463 c                                  be the difference between f and
103464 c                                  the previous best value of the
103465 c                                  objective function.
```

```
103466            20 gnew = 0.0
103467               sum = 0.0
103468               do 25 i=1,n
103469                  gnew = gnew+w(i)*g(i)
103470            25 sum = sum+g(i)**2
103471               if (ncalls.eq.1) go to 35
103472               fch = f-fmin
103473 c                                          store the values of x, f and g, if
103474 c                                             they are the best that have been
103475 c                                             calculated so far, and note g
103476 c                                             squared and the value of ncalls.
103477 c                                             test for convergence.
103478               if (fch) 35,30,50
103479            30 if (gnew/gmin.lt.-1.0) go to 45
103480            35 fmin = f
103481               gsqrd = sum
103482               nfopt = ncalls
103483               do 40 i=1,n
103484                  w(ixopt+i) = x(i)
103485            40 w(igopt+i) = g(i)
103486            45 if (sum.le.acc) go to 9005
103487 c                                          test if the value of maxfn allows
103488 c                                             another call of funct.
103489            50 if (ncalls.ne.maxfn) go to 55
103490               ier = 131
103491               go to 9000
103492            55 if (ncalls.gt.1) go to 100
103493 c                                          set dfpr to the estimate of the
103494 c                                             reduction in f given in the
103495 c                                             argument list, in order that the
103496 c                                             initial change to the parameters
103497 c                                             is of a suitable size. the value
103498 c                                             of stmin is usually the
103499 c                                             step-length of the most recent
103500 c                                             line search that gives the least
103501 c                                             calculated value of f.
103502               dfpr = dfpred
103503               stmin = dfpred/gsqrd
103504 c                                          begin the iteration
103505            80 iterc = iterc+1
103506 c                                          store the initial function value and
103507 c                                             gradient, calculate the initial
103508 c                                             directional derivative, and branch
103509 c                                             if its value is not negative. set
103510 c                                             sbound to minus one to indicate
103511 c                                             that a bound on the step is not
103512 c                                             known yet, and set nfbeg to the
103513 c                                             current value of ncalls. the
103514 c                                             parameter iretry shows the number
103515 c                                             of attempts at satisfying the beta
103516 c                                             condition.
103517               finit = f
103518               ginit = 0.0
103519               do 85 i=1,n
103520                  w(iginit+i) = g(i)
103521            85 ginit = ginit+w(i)*g(i)
103522               if (ginit.ge.0.0) go to 165
103523               gmin = ginit
103524               sbound = -1.0
103525               nfbeg = ncalls
103526               iretry = -1
103527 c                                          set stepch so that the initial
103528 c                                             step-length is consistent with the
103529 c                                             predicted reduction in f, subject
103530 c                                             to the condition that it does not
```

```
103531 c                                    exceed the step-length of the
103532 c                                    previous iteration. let stmin be
103533 c                                    the step to the least calculated
103534 c                                    value of f.
103535       stepch = amin1(stmin,abs(dfpr/ginit))
103536       stmin = 0.0
103537 c                                    call subroutine funct at the value
103538 c                                    of x that is defined by the new
103539 c                                    change to the step-length, and let
103540 c                                    the new step-length be step. the
103541 c                                    variable work is used as work
103542 c                                    space.
103543    90 step = stmin+stepch
103544       work = 0.0
103545       do 95 i=1,n
103546       x(i) = w(ixopt+i)+stepch*w(i)
103547    95 work = amax1(work,abs(x(i)-w(ixopt+i)))
103548       if (work.gt.0.0) go to 5
103549 c                                    terminate the line search if stepch
103550 c                                    is effectively zero.
103551       if (ncalls.gt.nfbeg+1) go to 115
103552       if (abs(gmin/ginit)-0.2) 170,170,115
103553 c                                    let spln be the quadratic spline
103554 c                                    that interpolates the calculated
103555 c                                    function values and directional
103556 c                                    derivatives at the points stmin
103557 c                                    and step of the line search, where
103558 c                                    the knot of the spline is at
103559 c                                    0.5*(stmin+step). revise stmin,
103560 c                                    gmin and sbound, and set ddspln to
103561 c                                    the second derivative of spln at
103562 c                                    the new stmin. however, if fch is
103563 c                                    zero, it is assumed that the
103564 c                                    maximum accuracy is almost
103565 c                                    achieved, so ddspln is calculated
103566 c                                    using only the change in the
103567 c                                    gradient.
103568   100 work = (fch+fch)/stepch-gnew-gmin
103569       ddspln = (gnew-gmin)/stepch
103570       if (ncalls.gt.nfopt) sbound = step
103571       if (ncalls.gt.nfopt) go to 105
103572       if (gmin*gnew.le.0.0) sbound = stmin
103573       stmin = step
103574       gmin = gnew
103575       stepch = -stepch
103576   105 if (fch.ne.0.0) ddspln = ddspln+(work+work)/stepch
103577 c
103578 c                                    test for convergence of the line
103579 c                                    search, but force at least two
103580 c                                    steps to be taken in order not to
103581 c                                    lose quadratic termination.
103582       if (gmin.eq.0.0) go to 170
103583       if (ncalls.le.nfbeg+1) go to 120
103584       if (abs(gmin/ginit).le.0.2) go to 170
103585 c                                    apply the test that depends on the
103586 c                                    parameter maxlin.
103587   110 if (ncalls.lt.nfopt+maxlin) go to 120
103588   115 ier = 129
103589       go to 170
103590 c                                    set stepch to the greatest change to
103591 c                                    the current value of stmin that is
103592 c                                    allowed by the bound on the line
103593 c                                    search. set gspln to the gradient
103594 c                                    of the quadratic spline at
103595 c                                    (stmin+stepch). hence calculate
```

```
103596 c                                   the value of stepch that minimizes
103597 c                                   the spline function, and then
103598 c                                   obtain the new function and
103599 c                                   gradient vector, for this value of
103600 c                                   the change to the step-length.
103601   120 stepch = 0.5*(sbound-stmin)
103602       if (sbound.lt.-0.5) stepch = 9.0*stmin
103603       gspln = gmin+stepch*ddspln
103604       if (gmin*gspln.lt.0.0) stepch = stepch*gmin/(gmin-gspln)
103605       go to 90
103606 c                                   calculate the value of beta that
103607 c                                   occurs in the new search
103608 c                                   direction.
103609   125 sum = 0.0
103610       do 130 i=1,n
103611   130 sum = sum+g(i)*w(iginit+i)
103612       beta = (gsqrd-sum)/(gmin-ginit)
103613 c                                   test that the new search direction
103614 c                                   can be made downhill. if it
103615 c                                   cannot, then make one attempt to
103616 c                                   improve the accuracy of the line
103617 c                                   search.
103618       if (abs(beta*gmin).le.0.2*gsqrd) go to 135
103619       iretry = iretry+1
103620       if (iretry.le.0) go to 110
103621 c                                   apply the test that depends on the
103622 c                                   parameter mxfcon.
103623 c                                   set dfpr to the predicted
103624 c                                   reduction in f on the next
103625 c                                   iteration.
103626   135 if (f.lt.finit) iterfm = iterc
103627       if (iterc.lt.iterfm+mxfcon) go to 140
103628       ier = 132
103629       go to 9000
103630   140 dfpr = stmin*ginit
103631 c                                   branch if a restart procedure is
103632 c                                   required due to the iteration
103633 c                                   number or due to the scalar
103634 c                                   product of consecutive gradients.
103635       if (iretry.gt.0) go to 10
103636       if (iterrs.eq.0) go to 155
103637       if (iterc-iterrs.ge.n) go to 155
103638       if (abs(sum).ge.0.2*gsqrd) go to 155
103639 c                                   calculate the value of gama that
103640 c                                   occurs in the new search
103641 c                                   direction, and set sum to a scalar
103642 c                                   product for the test below. the
103643 c                                   value of gamden is set by the
103644 c                                   restart procedure.
103645       gama = 0.0
103646       sum = 0.0
103647       do 145 i=1,n
103648       gama = gama+g(i)*w(irsdg+i)
103649   145 sum = sum+g(i)*w(irsdx+i)
103650       gama = gama/gamden
103651 c                                   restart if the new search direction
103652 c                                   is not sufficiently downhill.
103653 c
103654       if (abs(beta*gmin+gama*sum).ge.0.2*gsqrd) go to 155
103655 c
103656 c                                   calculate the new search direction.
103657       do 150 i=1,n
103658   150 w(i) = -g(i)+beta*w(i)+gama*w(irsdx+i)
103659       go to 80
```

```
103660 c                                              apply the restart procedure.
103661     155 gamden = gmin-ginit
103662         do 160 i=1,n
103663            w(irsdx+i) = w(i)
103664            w(irsdg+i) = g(i)-w(iginit+i)
103665     160 w(i) = -g(i)+beta*w(i)
103666         iterrs = iterc
103667         go to 80
103668 c                                              set ier to indicate that the search
103669 c                                                 direction is uphill.
103670     165 ier = 130
103671 c                                              ensure that f, x and g are optimal.
103672     170 if (ncalls.eq.nfopt) go to 180
103673         f = fmin
103674         do 175 i=1,n
103675            x(i) = w(ixopt+i)
103676     175 g(i) = w(igopt+i)
103677     180 if (ier.eq.0) go to 125
103678    9000 continue
103679         call uertst (ier,6hzxcgr )
103680    9005 return
103681         end
```

What is claimed is:

1. An ultrasound resonant spectrometer for use with a rectangular parallelepiped sample of a high dissipation material having an expected resonant response frequency range, comprising:
a sample holder structure for contacting corner portions of said sample;
a drive transducer assembly and a receive transducer assembly mounted on said holder for contacting said sample corner portions;
said drive and receive transducer assemblies including a piezoelectric transducer mounted on a membrane for weakly coupling said transducer to said sample holder structure and operatively contacting a material effective to remove system resonant responses at said transducer from said expected sample resonant response frequency range, effectively exciting an output response of said sample from said receive transducer assembly as said drive transducer assembly excites said sample over said expected resonant response frequency range.

2. An ultrasound resonant spectrometer according to claim 1, where said material is formed of a cylinder selected from diamond or beryllium and bonded to said transducer wherein a lowest resonant response of said transducer assembly is greater than the expected sample response.

3. An ultrasound resonant spectrometer according to claim 1, where said material is a powder effective to provide frictional damping for resonant responses of said transducer assembly within said expected sample resonant response frequency range.

4. An ultrasound resonant spectrometer according to claims 1, 2, or 3, further including an amplifier receiving said output response of sample from said receive transducer assembly, said amplifier receiving said output response through a cable connecting said receive transducer assembly and said amplifier and having a center signal conductor, a first shield isolated from ground, and a surrounding grounded second shield, said amplifier having a unity gain section for driving said isolated shield with a signal matching said output response to effectively eliminate capacitance effects from said connecting cable.

5. An ultrasound resonant spectrometer according to claim 4, wherein said amplifier has an input resistance and capacitance effective to define a substantially frequency - independent voltage divider with the capacitance of said receive transducer within said expected sample resonant response range.

6. In an ultrasound resonant spectrometer having a sample holder structure for contacting corner portions of a rectangular parallelepiped sample, a drive transducer assembly and a receive transducer assembly effective for contacting samples of low dissipation materials, said drive and receive transducer assemblies including a transducer mounted on a membrane for weakly coupling said transducer to said sample holder structure and operatively contacting a material effective to remove system resonant responses at said transducer from the expected sample resonant response frequency range.

7. A transducer assembly according to claim 6, where said material is formed of a cylinder selected from diamond or beryllium and bonded to said transducer wherein a lowest resonant response of said transducer assembly is greater than the expected sample response.

8. A transducer assembly according to claim 6, where said material is a powder effective to provide frictional damping for resonant responses of said transducer assembly within said expected sample resonant response frequency range.

* * * * *